(12) United States Patent
Ray

(10) Patent No.: US 6,306,170 B2
(45) Date of Patent: Oct. 23, 2001

(54) THREADED FUSION CAGE ANCHORING DEVICE AND METHOD

(75) Inventor: Charles D. Ray, Williamsburg, VA (US)

(73) Assignee: Tegementa, L.L.C., Williamsburg, VA (US)

( * ) Notice: Subject to any disclaimer, the term of this patent is extended or adjusted under 35 U.S.C. 154(b) by 0 days.

(21) Appl. No.: 09/790,751

(22) Filed: Feb. 22, 2001

Related U.S. Application Data

(63) Continuation of application No. 09/403,866, filed on Mar. 3, 2000, now abandoned.
(60) Provisional application No. 60/044,190, filed on Apr. 25, 1997.

(51) Int. Cl.[7] ...................................................... A61F 2/44
(52) U.S. Cl. ..................... 623/17.11; 623/17.16; 606/61
(58) Field of Search ............................. 623/17.11, 17.16; 606/71, 73, 61, 70, 69, 76, 77; 411/166

(56) References Cited

U.S. PATENT DOCUMENTS

| 5,092,893 | 3/1992 | Smith . |
| 5,108,395 | 4/1992 | Laurain . |
| 5,397,364 | 3/1995 | Kozak et al. . |
| 5,458,641 | 10/1995 | Ramirez Jimenez . |
| 5,534,031 | 7/1996 | Matsuzaki et al. . |
| 5,713,899 | 2/1998 | Marnay et al. . |
| 5,865,846 | 2/1999 | Bryan et al. . |
| 5,904,683 | 5/1999 | Pohndorf et al. . |
| 6,017,345 | * 1/2000 | Richelson ............................. 606/70 |
| 6,159,213 | * 12/2000 | Rogozinski ......................... 606/70 |
| 6,193,721 | * 2/2001 | Michelson ............................ 606/70 |
| 6,206,881 | * 3/2001 | Frigg et al. .......................... 606/69 |

* cited by examiner

Primary Examiner—Pedro Philogene

(57) ABSTRACT

The present disclosure is directed to an anchoring device and system for stabilizing adjacent vertebral joints. The anchoring device includes an anchoring plate adapted to be secured to at least one vertebral disc having a central portion, extended ends portions and at least one lateral extension. The central portion includes an anchoring nut for fastening the anchoring plate to a vertebral implant and the end portions include anchoring screws for fastening the anchoring plate to the at least one vertebral disc. The vertebral implant is preferably a threaded fusion cage, wherein the anchoring nut is rotatably fixed to both the anchoring plate and the threaded fusion cage. The anchoring device preferably includes the central portion and each extended end portion having at least one locking tab for rotatably locking the anchoring nut and anchoring screws. Additionally, the central portion further includes a plurality of projecting detents along an outer periphery thereof which mate with corresponding slots on the threaded fusion cage. The present disclosure is also directed to a method of implanting a vertebral implant.

16 Claims, 2 Drawing Sheets

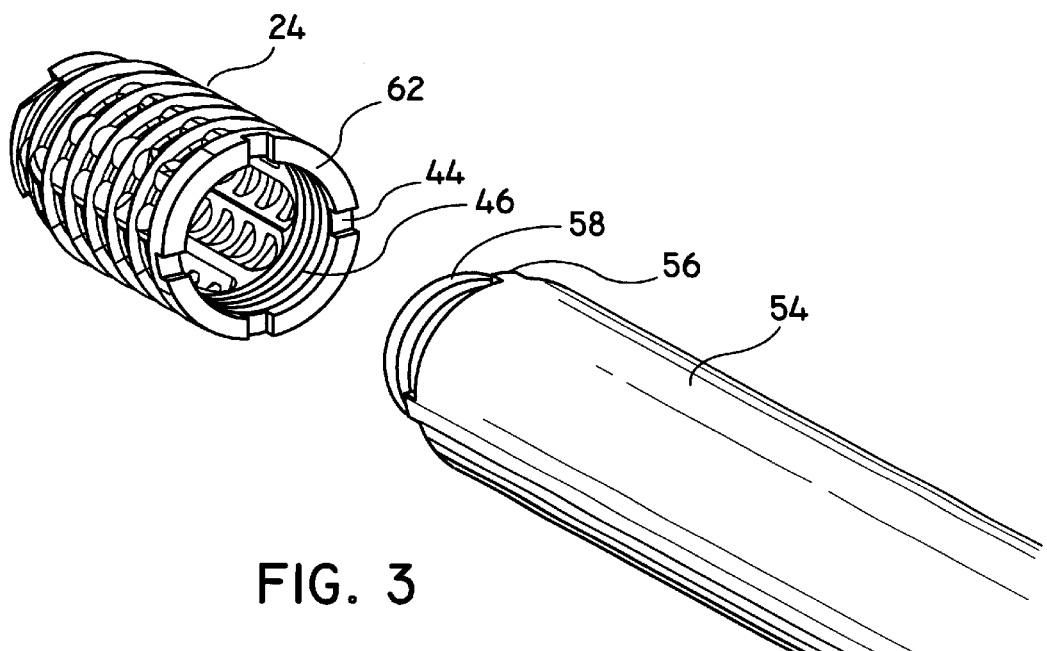
FIG. 3
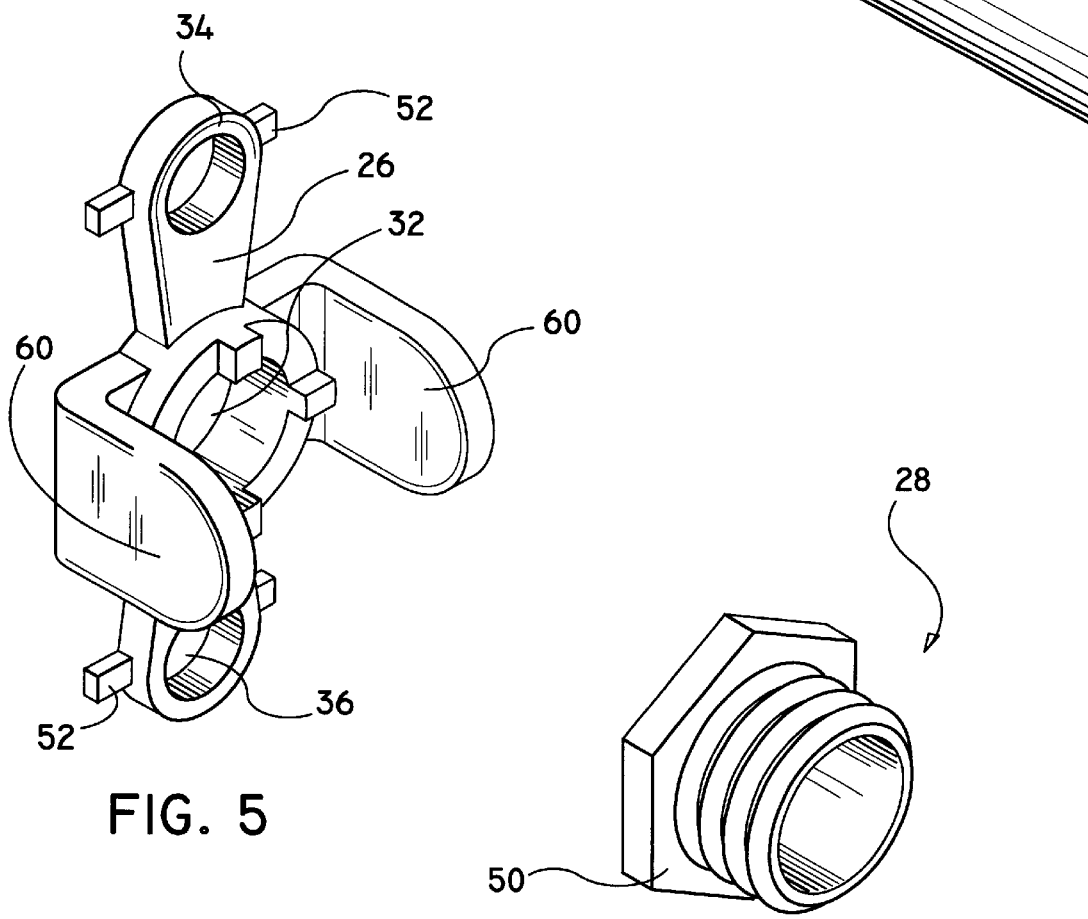
FIG. 5
FIG. 4

THREADED FUSION CAGE ANCHORING DEVICE AND METHOD

CROSS-REFERENCE TO RELATED APPLICATIONS

This patent application is a cont. of Ser. No. 09/403,866 filed Mar. 3, 2000 Abandoned and also claims the benefit of U.S. Provisional Application No. 60/044,190 filed Apr. 25, 1997.

TECHNICAL FIELD

The present disclosure concerns devices and methods for stabilizing fusion inserts placed for the purpose of fusing two adjacent joints such as vertebrae of the spine, and more particularly, to a threaded fusion cage anchoring device.

BACKGROUND OF RELATED ART

Degeneration of a joint such as a spinal segment by a deterioration of the hard and soft tissues of the joint complex may produce severe local or radiating pain when that segment is in motion. Typically joint complexes consist of two bony structures and an interposed flexible, movable portion. In the spine the bony structures are the vertebrae and the movable portion is the intervertebral disc. The disc is composed of a multilayered outer ligamentous belt, the annulus, constructed in concentric laminations rather like the plies of an automobile tire. In the core of the disc there is a small mass of flexible fibrogel, contained by the annulus ring. The fibrogel mass, the nucleus of the disc, is a hydrogel which on absorbing water exerts a substantial swelling pressure to lift the vertebra and balance the forces applied against the disc by gravity and surrounding muscular contractions. Therefore, the hydrogel is important for resisting potentially disruptive forces applied to the vertebrae.

Unfortunately, as the disc degenerates, the internally contained hydrogel begins to lose its water-binding ability and shrinks. This shrinkage leads to a loosening of the annulus fibers which permits an abnormal range of motion of the segment with buckling and delamination of the overlapping plies. Tears in as few as several layers of the approximately 12 to 20 concentric laminations of the annulus may permit a herniation of the pressured central nucleus material outward through the annulus defect.

Conventional procedures for treating degenerative vertebral discs involve fusing the discs together to stop all motion of the bone segments. The most efficient method of fusion places bone or a bone inducing substance inside a supporting device surgically implanted into the center of the disc. This supporting device construct will obliterate the degenerated nucleus, hold the bone material rigidly in position, protect the bone from collapse, extrusion or invasion by residual soft tissues of the disc and cause the opposing vertebrae to rapidly fuse together. The preferred intervertebral fusion device is a vertebral fusion cage. For example, U.S. Pat. No. 4,961,740 to Ray, contents of which are incorporated herein, discloses threaded vertebral fusion cages. The internal cavities of the cages are used to secure the bone graft material and to permit bone growth through and across the surgically emptied nucleus cavity between adjacent vertebrae.

As opposed to non-threaded fusion cages which are hammered or tapped into position, insertion of threaded vertebral fusion cages is made more efficient because the threaded outer surface permits easy adjustment of the depth and penetration of the cage into the disc space. The threaded outer surface also prevents dislodgment or expulsion of the cage. In addition, the graft bone packed within the threaded fusion cages presents or effuses through these perforations and comes into intimate contact with the bone of the adjacent vertebral bodies. When the cage is inserted into the bored or tapped intervertebral bed, the lateral walls of the cage are oriented horizontally and face the disc cavity. These lateral cage walls are blocked (i.e., contains no apertures) and therefore are a barrier against any potential ingrowth of residual disc tissue into the contained graft area which could interfere with or weaken the fusion formation of these adjacent vertebrae.

More recently, emphasis has been placed on securely fixating the fusion cage implant within the vertebrae. During a fusion cage implantation procedure, the surgeon may determine that sufficient stabilization of the space has not been achieved by implantation of the fusion cage alone. In such situations, additional instrumentation to improve the stability of the vertebrae and cage is required. Examples where additional stabilization procedures may be used include: the vertebral bone is weak, the cages do not fit tight enough in the vertebral space or the central concavity of the disc space is too deep to achieve good cage penetration along the anterior-posterior length of the disc space. In such cases, the surgeon ordinarily would be forced to place additional fusion instrumentation such as pedicle screws, rods or vertebral body plates to prevent cage dislodgment and improve the opportunity for a good fusion. This additional step in the surgical procedure increases the complexity, potential hazards and cost of the procedure. The embodiments of the present disclosure solve these and other associated problems and provides a simple and easily applied instrumentation to intraoperatively achieve increased cage fixation and disc space stability.

SUMMARY

The present disclosure is directed to an anchoring device and system for stabilizing adjacent vertebral joints. The anchoring device includes an anchoring plate adapted to be secured to at least one vertebral disc having a central portion, extended end portions and at least one lateral extension. The central portion includes an anchoring nut for fastening the anchoring plate to a vertebral implant and the end portions include anchoring screws for fastening the anchoring plate to the at least one vertebral disc. The vertebral implant is preferably a threaded fusion cage, wherein the anchoring nut is rotatably fixed to both the anchoring plate and the threaded fusion cage.

The anchoring device preferably includes the central portion and each extended end portion having at least one locking tab for rotatably locking the anchoring nut and anchoring screws. Additionally, the central portion further includes a plurality of projecting detents along an outer periphery thereof which mate with corresponding slots on the threaded fusion cage.

The present disclosure is also directed to a method of implanting an anchoring device to at least one vertebral disc having a vertebral implant. The method includes providing an anchoring plate having a central portion and extended end portions. The central portion includes an anchoring nut for fastening the anchoring plate to a vertebral implant and at least one locking tab along an outer periphery thereof. The end portions include anchoring screws for fastening the anchoring plate to at least one vertebral disc and at least one locking tab along an outer periphery thereof. The method further includes: situating the anchoring plate in a corresponding relationship to the at least one vertebral disc and the vertebral implant; fastening the anchoring nut to the vertebral implant; and fastening the anchoring screws to the at least one vertebral disc. The locking tabs are then positioned into engagement with the anchoring nut and anchoring screws.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

FIG. 3 is a perspective view illustrating a posterior aspect of a fusion cage and associated fusion cage inserting drive shaft;

FIG. 4 is a plan view of an anchoring nut associated with the anchoring device of the present disclosure; and FIG. 5 is a bottom plan view illustrating an anchoring device of an alternative embodiment according to the present disclosure.

DETAILED DESCRIPTION OF PREFERRED EMBODIMENTS

Figure 1:
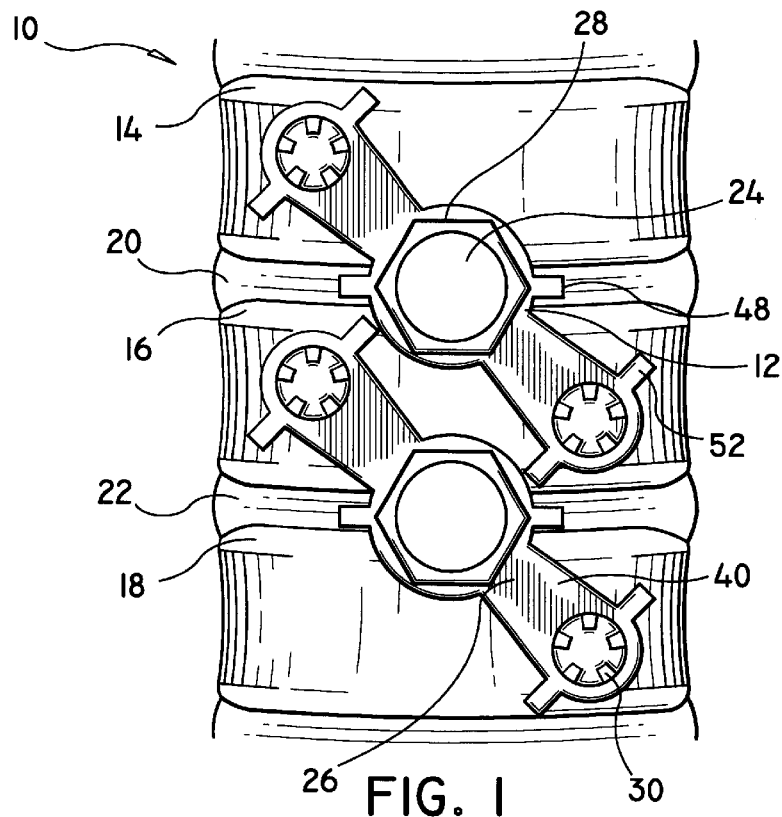
FIG. 1 is a view illustrating several adjacent spinal segments and two anchoring devices according to the present disclosure mounted to the spinal segments.

The preferred embodiments of the apparatus and methods disclosed herein are discussed in terms of orthopedic spinal fusion procedures and instrumentation. It is envisioned, however, that the disclosure is applicable to a wide variety of procedures including, but, not limited to joint repair, non-union fractures, facial reconstruction, spinal stabilization and the like. In addition, it is believed that the present method and instrumentation finds application in both open and minimally invasive procedures including endoscopic and arthroscopic procedures wherein access to the surgical site is achieved through a cannula or small incision.

The following discussion includes a description of the threaded fusion cage anchoring device utilized in performing a spinal fusion followed by a description of the preferred method for implanting the threaded fusion cage anchoring device in accordance with the present disclosure.

Reference will now be made in detail to the preferred embodiments of the disclosure, which are illustrated in the accompanying figures. Turning now to the figures, wherein like components are designated by like reference numerals throughout the various figures, attention is first directed to FIGS. 1 and 2.

An anterior view of a fused vertebral section 10 including two implanted anchoring devices 12 across three adjacent spinal segments 14, 16 and 18 are generally shown at FIG. 1. The spinal segments 14, 16 and 18, for instance, cervical spinal segments, are separated by two interposed disc spaces 20 and 22. Threaded fusion cages 24 are implanted between spinal segments 14 and 16 and spinal segments 16 and 18 and across the interposed disc spaces 20 and 22, respectively.

Figure 2:
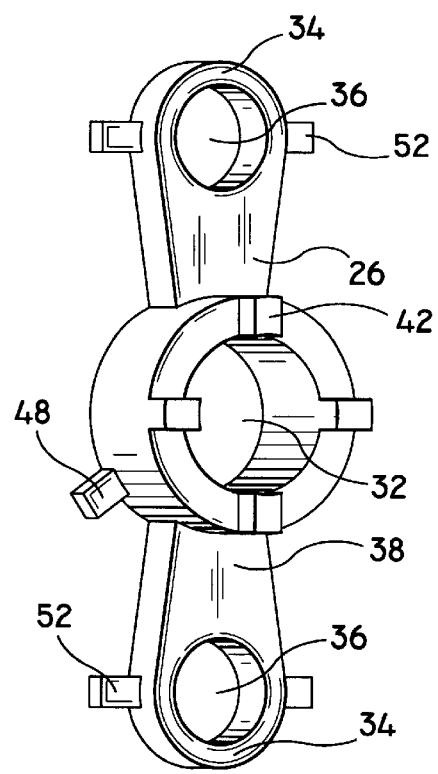
FIG. 2 is a bottom plan view of the anchoring device according to the present disclosure.

With particular reference to FIGS. 1–3, the anchoring device 12 of the present disclosure generally includes an anchoring plate 26, anchoring nut 28 and anchoring screws 30. Anchoring plate 26 is generally in the shape of a figure-eight and includes a large central bore 32 and extension arms 34. Each extension arm 34 includes at least one anchoring screw bore 36 for receiving anchoring screw 30. The anchoring device 12 of the present disclosure is preferably fabricated from a suitable biocompatible rigid material such as titanium and/or alloys of titanium, stainless steel, ceramic materials or rigid polymeric materials. Anchoring plate 26 includes a fusion cage mating side 38 (bottom, i.e., FIG.2) and an anchoring nut mating side 40 (top, i.e., FIG. 1). The fusion cage mating side 38 includes projecting detents or pins 42 for engaging slots 44 of fusion cage 24 (FIG. 3). The projecting detents 42 are preferably located along the outer periphery of central bore 32. The anchoring device 12 of the present disclosure and associated threaded fusion cage 24 may include any number of detents 42 and mating slots 44, wherein the higher quantity of projecting detents 42 and mating slots 44 provide for an optimal fixed relationship between the fusion cage 24 and the anchoring plate 26 without a large angular change in the implanted fusion cage 24 position. That is, the altering of the number of slots 44 of fusion cage 24, as well as, the mating projecting detents 42 of anchoring plate 26 will incrementally alter the angular relationship between the anchoring plate 26 and fusion cage 24. As such, minor angular changes in the orientation of the anchoring plate 26 with respect to the fusion cage 24 is beneficial so that the initial optimal depth of penetration of implanted fusion cage 24 into the joint space need not be markedly altered from the possible rotation attributable to the implantation of anchoring device 12.

As best depicted in FIG. 1, the orientation or angular displacement of the anchoring plate 26 relative to the longitudinal axis of the spinal column, may be altered from 0 to 80 degrees as needed to provide appropriate stability to the fusion cage 24 relative to the adjacent vertebrae. This broad angular displacement assures a safe positioning of the anchoring plate 26 relative to certain anatomical structures, such as, the vertebral end plate, nearby traversing nerves or bony obstructions. In this regard, when a pair of fusion cages 24 has been implanted at the same level, the anchoring plates 26 are preferably set substantially parallel to each other. Hence, having a broad angular displacement allows the angulation between each anchoring plate 26 to be altered in order to obtain optimal anchoring screw 30 placement in the vertebral bodies. Similarly, when two single cages 24 or a pair of cages 24 are placed at adjacent spinal levels, the common angulation of the anchoring plates 26 may be altered for optimal anchoring screw 30 placement into the adjacent vertebral bodies. Both the cages 24 and anchoring plates 26 may be placed by an anterior or posterior surgical approach to the lumbar spine. However, in the thoracic and cervical spinal areas an anterior method alone is recommended.

With particular reference to FIGS. 1, 2 and 4, the anchoring device 12 of the present disclosure is placed over the implanted fusion cages 24 and attached to each fusion cage 24 with a threaded anchoring nut 28 which screws into matching threads 46 inside the inner periphery of fusion cage 24. Once installed, anchoring nut 28 is prohibited from loosening by a plurality of malleable nut locking tabs 48 positioned on opposing sides of the central bore 32 of anchoring plate 26. The bending of the nut locking tabs 48 over the anchoring nut 28 will engage at least one flat portion of the anchoring nut collared head 50 and thereby prevent the anchoring nut 28 from rotating and becoming loose. The extension arms 34 of anchoring plate 26 include anchoring screw bores 36 through which slotted head anchoring screws 30 are passed and tightened into the vertebral bodies at convenient and safe locations. Similarly, the anchoring screws 30 are prevented from unscrewing by a plurality of malleable screw locking tabs 52 placed on opposing sides of the anchoring screw bores 36 on extension arms 34. The screw locking tabs 52 are oriented so that at least one of them will firmly mate with at least one slot located on the head of anchoring screws 30 when locking tabs 52 are bent over anchoring screws 30.

The anchoring device 12 provides the additional support needed to fully stabilize the fusion cage 24 relative to spinal segments 14, 16 and 18. By crossing the interposed disc space 20 and 22 and attaching the anchoring screws 30 to the vertebral bodies at an extended distance from fusion cage 24, a substantial increase in mechanical fixation strength is provided. Essentially, the anchoring device 12 keeps the vertebrae from moving apart and therefore from distracting away from the fusion cage 24 as postoperative spinal motions occur. Further, the anchoring plate 26 significantly improves the initial overall rigidity of the fusion cage system.

With reference to FIG. 3, a fusion cage 24 inserting drive shaft 54 for seating a threaded fusion cage 24 inside a bore made between adjacent surfaces of a spinal segment is shown. A plurality of slots 44 on the outer edge 62 of the fusion cage 24 match projecting tabs 56 on drive shaft 54. The fusion cage 24 attaches to a retractable central threaded coupler 58 which rotates freely within the drive shaft 54. The fusion cage slots 44 mate with the projecting tabs 56 of drive shaft 54. Upon rotation of drive shaft 54, the threaded coupler 58 engages the matching fusion cage threads 46 located along an inner periphery of fusion cage 24. The mated slots 44 and projecting tabs 56 are used to rotatably drive the fusion cage 24 into position after which the threaded coupler 58 is unscrewed releasing both the drive shaft 54 and threaded coupler 58 from the fusion cage 24. In the cases where positioning of fusion cage 24 needs further adjustment, the drive shaft 54 may be mated to the fusion cage 24 via projecting tabs 56 and slots 44 to torque the fusion cage 24 into a final position without the necessity of firmly reattaching the threaded coupler 58 to the fusion cage 24.

With particular reference to FIG. 5, an additional embodiment of the anchoring plate 26 is shown, wherein like components which correspond to those of previous embodiments described herein are designated by like reference numerals. Anchoring plate 26 further includes additional lateral extensions or tangs 60 for further stabilizing the interposed disc spaces 20 and 22 by being forced into the spaces 20 and 22 as the anchoring nut 28 is tightened onto anchoring plate 26 and into fusion cage 24. The space between the margins of lateral tangs 60 may accommodate additional bone growth material such as cancellous or soft bone from another human (allograft) or from the same patient (autograft) which serves to provide a better fusion of spinal segments 14, 16 and 18.

Implantation of the Anchoring Device

The implantation of the anchoring device 12 of the present disclosure will now be described with respect to a single anchoring device 12 although multiple anchoring devices 12 can be implanted across one or more vertebral discs or spinal segments 14, 16 and 18. A standard surgical approach is used to gain access to the surface of the vertebral bodies to be fused. This may consist of an anterior approach in the neck and thoracic spine or an anterior or posterior approach in the lumbar spine. One or more bores are drilled into selected intervertebral spaces and tissue debris is cleaned out therefrom. For some fusion cage implants, the bore may be tapped to match the threaded portion of the fusion cages. In other cases, a self-tapping fusion cage may be used and no threading will be required.

As shown generally at FIG. 3, a threaded fusion cage 24 having slots 44 along its outer edge 62 is mated to projecting tabs 56 on the tip of the drive shaft 54, wherein the threaded coupler 58 is threaded onto the inner fusion cage threads 46 of fusion cage 24 to secure the fusion cage 24 to the drive shaft 54 during insertion thereof within the intervertebral spaces. Next, the fusion cage 24 is screwed into its optimal position in the prepared intervertebral bore and the threaded coupler 58 and drive shaft 54 are detached.

The placement of anchoring device 12 is dependent upon the actual location of the implanted fusion cage 24. If a single fusion cage 24 or alternatively a pair of fusion cages 24 are implanted at multiple vertebral levels, then the orientation of the anchoring plates 26 will be in parallel pairs throughout the multiple fused vertebral segments. The projecting detents 42 located along the mating surface 38 of anchoring plate 26 mates with equivalently spaced slots 44 located on the outer edge 62 of the implanted fusion cage 24. A minor angular adjustment is made in the orientation of the anchoring plate 26 and fusion cage 24 relative to the longitudinal axis of the spine to maintain clearance of any anatomical structures. This angular adjustment requires only a few degrees of change from the initial position of the fusion cage 24. The anchoring plate 26 may be bent slightly, before or after being attached to the fusion cage 24, to conform with the curving surface of the vertebral bodies or to establish clearance from other adjacent structures.

Once an anchoring plate 26 is positioned over the implanted fusion cage 24, the anchoring nut 28 is passed through the central bore 32 of the anchoring plate 26 and screwed into the corresponding mating fusion cage threads 46 portion of the implanted fusion cage 24. Since the anchoring device 12 and fusion cage 24 can include a plurality of projecting detents 42 and mating slots 44, the anchoring plate 26 can be incrementally rotated to bring the anchoring plate 26 into its most advantageous position relative to the fusion cage 24 position. The rotation or adjusting of the anchoring plate 26 with respect to the fusion cage 24 is performed prior to tightening the anchoring nut 28 to the anchoring plate 26 and fusion cage 24. Pilot holes or bores are then drilled into the vertebrae through the anchoring screw bores 36 of extension arms 34. The extension arms 34 are next fitted with anchoring screws 30 of the appropriate length through bores 36 which are screwed and anchored into the vertebral bone. Both nut locking tabs 48 and screw locking tabs 52 are bent over the edges of anchoring nut 28 and the slots of anchoring screw 30, respectively, to prevent either from loosening or unscrewing. Bone inducing material is then packed inside fusion cage 24, through central bore 32 and the center of anchoring nut 28. Alternatively, bone inducing material may be packed into fusion cage 24 prior to insertion.

With respect to the alternative embodiment of anchoring device 12 depicted at FIG. 5, wherein like components and methods correspond to those of previously described embodiments described herein and are designated by like reference numerals. The implantation of anchoring plate 26 further includes the addition of bone inducing material laterally placed along fusion cage 24 prior to attaching anchoring plate 26 to fusion cage 24.

It will be understood that various modifications may be made to the embodiments disclosed herein. For example, the anchoring device 12 of the present disclosure may include any number of nut locking tabs 48 and screw locking tabs 52 to better secure each nut 28 and screw 30, respectively. Also, anchoring device 12 may include one or more extension arms 34 radially displaced along an angular relationship from central bore 32 which would provide better stabilization of the anchoring device 12, fusion cage 24 and associated bone segments 14, 16 and 18. Therefore, the above description should not be construed as limiting, but merely as exemplifications of preferred embodiments. Those skilled in the art will envision other modifications within the scope and spirit of the claims appended hereto.

What is claimed is:

1. An anchoring device for use with a vertebral implant, said device comprising:

an anchoring plate having a central portion and at least one extended end portion;

the central portion configured for attachment to a vertebral implant; and each end portion including an anchoring fastener and at least one locking tab adapted to engage said fastener and hold it in a fixed relationship to said anchoring plate, wherein the anchoring plate is adapted to be joined to a bony segment.

2. The anchoring device according to claim 1, including two extended end portions.

3. The anchoring device according to claim 1, wherein the vertebral implant is a threaded fusion cage.

4. The anchoring device according to claim 1, wherein the anchoring fastener is a bone screw.

5. The anchoring device according to claim 1, wherein the central portion further includes at least one locking tab.

6. The anchoring device according to claim 1, wherein the central portion further includes a plurality of projecting detents for engaging said implant.

7. The anchoring device according to claim 1, wherein the anchoring plate further includes at least one lateral extension.

8. A system for stabilizing adjacent vertebral bodies comprising:

a vertebral implant adapted to be secured between adjacent vertebral bodies;

an anchoring plate adapted to be secured to the adjacent vertebral bodies, the anchoring plate having a central portion and extended end portions;

the central portion including an anchoring nut for fastening the anchoring plate to the vertebral implant; and the end portion including anchoring screws for fastening the anchoring plate to the adjacent vertebral bodies.

9. The anchoring system according to claim 8, wherein the vertebral implant is a threaded fusion cage.

10. The anchoring system according to claim 9, wherein the anchoring nut is rotatably fixed to the anchoring plate and the threaded fusion cage.

11. The anchoring system according to claim 8, wherein each end portion is fixedly attached to a vertebral disc.

12. The anchoring system according to claim 8, wherein the central portion and each extended end portion further includes at least one locking tab.

13. The anchoring device according to claim 8, wherein the central portion further includes a plurality of projecting detents for engaging said implant.

14. The anchoring system according to claim 8, wherein the anchoring plate further includes at least one lateral extension.

15. A method of implanting a vertebral implant comprising the steps of:

inserting a vertebral implant between adjacent vertebrae;

positioning an anchoring plate in a corresponding relationship to the vertebral implant and the adjacent vertebrae, the anchoring plate including a central portion and extended ends portions, the central portion including an anchoring nut for fastening the anchoring plate to the vertebral implant, and the end portions including anchoring screws for fastening the anchoring plate to portions of the adjacent vertebrae;

fastening the anchoring nut to the vertebral implant; and fastening the anchoring screws to the portions of the adjacent vertebrae.

16. The method of implanting a vertebral implant according to claim 15, wherein the anchoring plate includes at least one locking tab along an outer periphery of the central portion and the extended end portions, and further including the step of positioning the locking tabs into engagement with the anchoring nut and anchoring screws.

* * * * *